United States Patent [19]

Resconi et al.

[11] Patent Number: 5,786,495
[45] Date of Patent: Jul. 28, 1998

[54] BRIDGED BIS-FLUORENYL METALLOCENES, PROCESS FOR THE PREPARATION THEREOF AND USE THEREOF IN CATALYSTS FOR THE POLYMERIZATION OF OLEFINS

[75] Inventors: Luigi Resconi, Ferrara, Italy; Robert L. Jones, Elkton, Md.

[73] Assignee: Montell Technology Company BV, MS Hoofddorp, Netherlands

[21] Appl. No.: 609,721

[22] Filed: Mar. 1, 1996

[30] Foreign Application Priority Data

Mar. 3, 1995 [IT] Italy ................ MI95A0410

[51] Int. Cl.⁶ ............... C07F 9/00; C07F 17/00; C07F 7/00; C07F 7/28
[52] U.S. Cl. ............... 556/11; 556/12; 556/20; 556/43; 556/53; 556/56; 556/81; 526/160; 526/943; 502/103; 502/117
[58] Field of Search ............... 556/11, 43, 53, 556/56, 58, 12, 20, 81; 534/11, 15

[56] References Cited

U.S. PATENT DOCUMENTS

| | | | |
|---|---|---|---|
| 4,668,773 | 5/1987 | Marks et al. | 534/15 |
| 5,120,867 | 6/1992 | Welborn, Jr. | 556/53 |
| 5,401,817 | 3/1995 | Palackal et al. | 556/11 |
| 5,436,305 | 7/1995 | Alt et al. | 556/58 |
| 5,504,223 | 4/1996 | Rosen et al. | 556/53 |
| 5,571,880 | 11/1996 | Alt et al. | 556/58 |
| 5,585,509 | 12/1996 | Langhauser et al. | 556/56 |

FOREIGN PATENT DOCUMENTS

| | | |
|---|---|---|
| 0 512 554 A2 | 11/1992 | European Pat. Off. . |
| 0 524 624 A2 | 1/1993 | European Pat. Off. . |
| 0 530 908 A1 | 3/1993 | European Pat. Off. . |
| 0 604 908 A2 | 7/1994 | European Pat. Off. . |
| 0 604 917 A2 | 7/1994 | European Pat. Off. . |
| 0 628 565 A1 | 12/1994 | European Pat. Off. . |
| 0 632 066 A1 | 1/1995 | European Pat. Off. . |
| 1-249782 | 10/1989 | Japan . |

Primary Examiner—Mark L. Bell
Assistant Examiner—J. Pasterczyk
Attorney, Agent, or Firm—Bryan Cave LLP

[57] ABSTRACT

Metallocene compounds of a Group 4 or 5 metal having two fluorenyl ligands bridged with a single silicon or germanium atom, said atom having two substituent groups containing a total of at least four carbon atoms, are useful as catalyst components for the polymerization of olefins. Particularly, it is possible to prepare high molecular weight atactic polypropylene with improved yields with respect to the known catalysts.

6 Claims, 1 Drawing Sheet

Fig.1

BRIDGED BIS-FLUORENYL METALLOCENES, PROCESS FOR THE PREPARATION THEREOF AND USE THEREOF IN CATALYSTS FOR THE POLYMERIZATION OF OLEFINS

BACKGROUND OF THE INVENTION

1. Field of the invention

The present invention relates to fluorenyl compounds, to the corresponding bridged bis-fluorenyl metallocenes and to their use as catalyst components in processes for the polymerization of olefins.

2. Description of related art

Many metallocene compounds are known to be active as catalyst components in the olefin polymerization reactions. A particular class of these metallocenes is that of stereorigid metallocene compounds having two cyclopentadienyl ligands joined by means of a bridging group which gives stereo-rigidity to the molecule. These compounds, which are generally referred to as bridged metallocenes, can be prepared from the corresponding bridged ligands.

While compounds having two bridged ligands of the indenyl type are widely known, there are only a few disclosures of compounds having two bridged fluorenyl groups.

In Japanese Patent Application Publication No. 1 249 782, it is described the preparation of the potassium salt of the bis(fluorenyl)dimethylsilane to be used for preparing organo-lantanide hydrides. These compounds are useable as catalysts for the hydrogenation of olefins of every type and for the polymerization of ethylene.

A process for the preparation of bridged fluorenyl-containing compounds is disclosed in EP-A-512,554. With this process 1,2-bis(9-fluorenyl)ethane, 1,3-bis(9-fluorenyl)propane, bis(9-fluorenyl) methane, 1,2-bis(9-fluorenyl)-2-methyl-ethane and bis(9-fluorenyl)-dimethyl-silane were prepared.

Bridged bis-fluorenyl compounds are disclosed in EP-A-524,624. A number of ethylidene, propylidene, methylethylidene and, dimethyl-silyl-bridged bis-fluorenyl compounds were prepared.

EP-A-604,908 discloses a class of bis-fluorenyl compounds bridged with a one-atom-bridge. Only dimethylsilyl-bridged bis-fluorenyl compounds are exemplified. These metallocenes are useful as catalyst components for the polymerization of olefins and, expecially, for the preparation of high molecular weight atactic polypropylene.

Diphenyl-silyl and dimethyl-tin bridged bis-fluorenyl metallocenes are disclosed in EP-A-628,565. These compounds are used in the preparation of isotactic polypropylene.

SUMMARY OF THE INVENTION

New metallocenes having two bridged fluorenyl rings which can be advantageously used as catalytic components for the polymerization of olefins and, expecially, for the preparation of high molecular weight atactic polypropylene with improved yields, have been surprisingly found.

Therefore, in accordance with an aspect of the present invention, there are provided metallocene compounds having two fluorenyl ligands bridged with a single silicon or germanium atom, said atom having two substituent groups containing a total of at least four carbon atoms.

According to another aspect of the present invention there is provided a method for the preparation of the above described metallocene compounds.

Still further in accordance with the present invention, there are provided bis-fluorenyl ligands bridged with a single silicon or germanium atom, said atom having two substituent groups containing a total of at least four carbon atoms.

Furthermore, according to another aspect of the present invention, there are provided catalysts for the polymerization of olefins comprising the bis-fluorenyl metallocenes of the invention.

According to a still further aspect of the present invention there is provided a process for the polymerization of olefins comprising the polymerization reaction of at least an olefinic monomer in the presence of such catalysts.

DESCRIPTION OF THE PREFERRED EMBODIMENTS

The metallocene compounds according to the present invention are those of the formula (I):

wherein each $R^1$, same or different, is an hydrogen atom, a $C_1$–$C_{20}$ alkyl radical, a $C_3$–$C_{20}$ cycloalkyl radical, a $C_2$–$C_{20}$ alkenyl radical, a $C_6$–$C_{20}$ aryl radical, a $C_7$–$C_{20}$ alkylaryl radical, or a $C_7$–$C_{20}$ arylalkyl radical, and optionally two adjacent $R^1$ substituents can form a cycle comprising from 5 to 8 carbon atoms and, furthermore, the $R^1$ substituents can contain Si or Ge atoms; the E bridging group is selected from a >$SiR^3{}_2$ or >$GeR^3{}_2$ group, wherein each $R^3$, same or different, is a $C_1$–$C_{20}$ alkyl, $C_3$–$C_{20}$ cycloalkyl, $C_2$–$C_{20}$ alkenyl, $C_6$–$C_{20}$ aryl, $C_7$–$C_{20}$ alkylaryl or $C_7$–$C_{20}$ arylalkyl radical, optionally containing heteroatoms, or the two $R^3$ substituents can be joined to form a cycle comprising up to 8 atoms, at least four total carbon atoms being contained in the two $R^3$ substituents; M is an atom of a transition metal belonging to the group 3, 4 or 5 or to the Lanthanide or Actinide group of the Periodic Table of the Elements (new IUPAC version); each Z, same or different, is an halogen atom, an —OH, —SH, $R^4$, —$OR^4$, —$SR^4$, —$NR^4{}_2$ or $PR^4{}_2$ group, wherein $R^4$ is defined as $R^1$. Preferred substituents $R^1$ are hydrogen atoms, $C_1$–$C_{10}$, more preferably $C_1$–$C_3$, alkyl radicals; $C_3$–$C_{10}$, more preferably $C_3$–$C_6$, cycloalkyl radicals; $C_2$–$C_{10}$, more preferably $C_2$–$C_3$, alkenyl radicals, $C_6$–$C_{10}$ aryl radicals, $C_7$–$C_{10}$ alkylaryl radicals or $C_7$–$C_{10}$ arylalkyl radicals. Alkyl radicals can be linear or branched, in addition to cyclic.

In the E bridging group, the $R^3$ substituents are preferably $C_2$–$C_{10}$, more preferably $C_4$–$C_8$, alkyl groups. Particularly preferred E bridging groups are the >SiR³₂ groups, such as the bis(n-butyl)silanediyl group.

The transition metal M is preferably selected from titanium, zirconium and hafnium, more preferably it is zirconium.

Substituents Z are preferably halogen atoms or R⁴ groups. More preferably, they are chlorine atoms or methyl radicals.

Non limitative examples of metallocenes of formula (I) according to the invention are: diethylsilanediylbis(fluorenyl)titanium dichloride, diethylsilanediylbis(fluorenyl)zirconium dichloride, diethylsilanediylbis(fluorenyl)hafnium dichloride, diethylsilanediylbis(fluorenyl)titanium dimethyl, diethylsilanediylbis(fluorenyl) zirconium dimethyl, diethylsilanediylbis(fluorenyl)hafnium dimethyl, di(n-propyl)silanediylbis(fluorenyl)titanium dichloride, di(n-propyl)silanediylbis(fluorenyl)zirconium dichloride, di(n-propyl)silanediylbis(fluorenyl)hafnium dichloride, di(n-propyl)silanediylbis(fluorenyl)titanium dimethyl, di(n-propyl)silanediylbis(fluorenyl)zirconium dimethyl, di(n-propyl)silanediylbis(fluorenyl)hafnium dimethyl, di(n-butyl)silanediylbis(fluorenyl)titanium dichloride, di(n-butyl)silanediylbis(fluorenyl)zirconium dichloride, di(n-butyl)silanediylbis(fluorenyl)hafnium dichloride, di(n-butyl)silanediylbis(fluorenyl)titanium dimethyl, di(n-butyl)silanediylbis(fluorenyl)zirconium dimethyl, di(n-butyl)silanediylbis(fluorenyl)hafnium dimethyl, methyl(n-butyl)silanediylbis(fluorenyl)titanium dichloride, methyl(n-butyl)silanediylbis(fluorenyl)zirconium dichloride, methyl(n-butyl)silanediylbis(fluorenyl)hafnium dichloride, methyl(n-butyl)silanediylbis(fluorenyl)titanium dimethyl, methyl(n-butyl)silanediylbis(fluorenyl)zirconium dimethyl, methyl(n-butyl)silanediylbis(fluorenyl)hafnium dimethyl, methyl(n-hexyl)silanediylbis(fluorenyl)titanium dichloride, methyl(n-hexyl)silanediylbis(fluorenyl)zirconium dichloride, methyl(n-hexyl)silanediylbis(fluorenyl)hafnium dichloride, methyl(n-octyl)silanediylbis(fluorenyl)titanium dichloride, methyl(n-octyl)silanediylbis(fluorenyl)zirconium dichloride, methyl(n-octyl)silanediylbis(fluorenyl)hafnium dichloride, diethylgermandiylbis(fluorenyl)titanium dichloride, diethylgermandiylbis(fluorenyl)zirconium dichloride, diethylgermandiylbis(fluorenyl)hafnium dichloride, diethylgermandiylbis(fluorenyl)titanium dimethyl, diethylgermandiylbis(fluorenyl)zirconium dimethyl, diethylgermandiylbis(fluorenyl)hafnium dimethyl, diethylsilanediylbis(1-methylfluorenyl)titanium dichloride, diethylsilanediylbis(1-methylfluorenyl) zirconium dichoride, diethylsilanediylbis(1-methylfluorenyl)hafnium dichloride, diethylsilanediylbis(1-methylfluorenyl)titanium dimethyl, diethylsilanediylbis(1-methylfluorenyl)zirconium dimethyl, diethylsilanediylbis(1-methylfluorenyl) hafnium dimethyl.

The metallocene compounds of formula (I) can be prepared from the corresponding fluorenyl ligands with a process which comprises the following steps:

(a) the reaction of a compound of formula (II):

wherein substituents R¹, the same or different from each other, are defined as above, with a compound able to form the anion of formula (III):

and thereafter with a compound of formula EX₂, wherein R² is defined as above, and the substituents X, same or different from each other, are halogen atoms, thus obtaining a compound of formula (IV):

(b) the subsequent reaction of the compound of formula (IV) obtained at point (a) with a compound able to form the dianion of formula (V):

and thereafter with a compound of formula MX'₄ wherein M is defined as above and the substituents X' are halogen atoms, thus obtaining the compound of formula (VI):

(VI)

and finally, (c) in the case at least one Z in the metallocene of formula (I) to be prepared is different from halogen, the substitution of at least one substituent X' in the compound of formula (VI) with at least one Z different from halogen.

Non limitative examples of compounds able to form anionic compounds of formula (III) and (V) are methyllithium, n-butyllithium, potassium hydride, metallic sodium or potassium.

Non limitative examples of compounds of formula $EX_2$ are diethyldichlorosilane, di(n-propyl)dichlorosilane, di(n-butyl)dichlorosilane, methyl (n-butyl) dichlorosilane, methyl (n-hexyl)dichlorosilane, methyl(n-octyl) dichlorosilane,f methyl(2-bicycloheptyl) dichlorosilane, methyl(3,3,3-trifluoropropyl) dichlorosilane, diethyldichlorogermanium. Di(n-butyl) dichlorosilane is particularly interesting.

Non limitative examples of compounds of formula $MX'_4$ are titanium tetrachloride, zirconium tetrachloride, hafnium tetrachloride. Particularly interesting is zirconium tetrachloride.

The substitution reaction of substituents X' in the compound of formula (VI) with substituents Z different from halogen is carried out by generally used methods. For example, when substituents X are alkyl groups, the compound of formula (VI) can be reacted with alkylmagnesium halides (Grignard reagents) or with lithioalkyl compounds.

According to an embodiment of the process according to the invention, the synthesis of the ligand of formula (IV) is suitably performed by adding a solution of an organic lithium compound in an aprotic solvent to a solution of the compound (II) in an aprotic solvent. Thus, a solution containing the compound (II) in the anionic form is obtained and this is added to a solution of the compound of formula $EXhd 2$ in an aprotic solvent.

From the solution obtained by working as above described, the ligand of formula (IV) is separated by common organic chemistry. The thus separed ligand is dissolved or suspended in an aprotic polar solvent, and to this solution a solution of an organic lithium compound in an aprotic solvent is added. The ligand (V) is thus obtained and is separated, dissolved or suspended in an aprotic polar solvent and thereafter added to a suspension of the compound $MX'_4$ in an apolar solvent. At the end of the reaction the solid product obtained is separated from the reaction mixture by generally used techniques.

During the whole process, the temperature is kept between —180° and 80° C. and, preferably, between 0° and 40° C.

As apolar solvents hydrocarbon solvents such as pentane, hexane, benzene and the like can be suitably used.

Non limitative examples of aprotic polar solvents are tetrahydrofurane, dimethoxyethane, diethylether, toluene, dichloromethane and the like.

The metallocene ligands according to the present invention are those of the formula (IV):

(IV)

wherein substituents $R^1$ and the E bridging group are defined as above, which are intermediate ligands that can be used for preparing metallocenes of formula (I).

Non limitative examples of compounds of formula (IV) according to the invention are diethylbis (fluorenyl) silane, di(n-propyl)bis(fluorenyl)silane, di(n-butyl)bis(fluorenyl) silane, methyl(n-hexyl)bis(fluorenyl)silane, methyl(n-octyl) bis(fluorenyl)silane, methyl(2-bicycloheptyl)bis-(fluorenyl) silane, methyl(3,3,3-trifluoropropyl)bis-(fluroenyl) silane, diethylbis (fluorenyl) germanium, diethylbis (1-methylfluorenyl)silane.

The present invention further relates to a catalyst for the polymerization of olefins, comprising the product of the reaction between:

(A) a metallocene compound of formula (I), optionally as reaction product with an aluminium organo-metallic compound of formula $AlR^5{}_3$ or $Al_2R^5{}_6$, wherein substituents $R^5$, the same or different from each other, are defined as $R^1$ or are halogen atoms, and (B) an alumoxane, optionally mixed with an aluminium organo-metallic compound of formula $AlR^5{}_3$ or $Al_2R^5{}_6$, wherein substituents $R^5$, the same or different from each other, are defined as above, or one or more compounds able to give a metallocene alkyl cation.

The molar ratio between aluminium and the metal of the metallocene is comprised between about 10:1 and about 5000:1, and preferably between 100:1 and 4000:1.

The alumoxane used as component (B) can be obtained by reaction between water and an organometallic compound of aluminium of formula $AlR^5{}_3$ or $Al_2R^5{}_6$, wherein substituents $R^5$, the same or different from each other, are defined as above, with the provision that at least one $R^5$ is different from halogen. In that case, these are reacted in molar ratios Al/water comprised between about 1:1 and 100:1.

Non limitative examples of aluminium compounds of formula $AlR^5{}_3$ or $Al_2R^5{}_6$ are:

| | | | |
|---|---|---|---|
| Al(Me)₃, | Al(Et)₃, | AlH(Et)₂, | Al(iBu)₃, |
| AlH(iBu)₂, | Al(iHex)₃, | Al(iOct)₃, | AlH(iOct)₂, |
| Al(C₆H₅)₃, | Al(CH₂C₆H₅)₃, | Al(CH₂CMe₃)₃, | Al(CH₂SiMe₃)₃, |
| Al(Me)₂iBu, | Al(Me)₂Et, | AlMe(Et)₂, | AlMe(iBu)₂, |
| Al(Me)₂iBu, | Al(Me)₂Cl, | Al(Et)₂Cl, | AlEtCl₂, |
| Al₂(Et)₃Cl₃, | | | | wherein Me=methyl, Et=ethyl, iBu=isobutyl, iHex=isohexyl, iOct=2,4,4-trimethyl-pentyl.

Among the above mentioned aluminium compounds, trimethylaluminium and triisobutylaluminium are preferred.

The alumoxane used in the catalyst according to the invention is believed to be a linear, branched or cyclic compound, containing at least one group of the type:

wherein substituents $R^6$, the same or different from each other, are $R^5$ or a group —O—$Al(R^6)_2$.

Examples of alumoxanes suitable for use according to the present invention are methylalumoxane (MAO), isobutylalumoxane (TIBAO) and 2,4,4-trimethyl-pentylalumoxane (TIOAO), the methylalumoxane being preferred. Mixtures of differents alumoxanes are suitable as well.

Non limitative examples of compounds able to form a metallocene alkyl cation are compounds of formula $Y^+Z^-$, wherein $Y^+$ is a Bronsted acid, able to give a proton and to react irreversibly with a substituent Z of the metallocene of formula (I), and $Z^-$ is a compatible anion, which does not coordinate, which is able to stabilize the active catalytic species which originates from the reaction of the two compounds and which is sufficiently labile to be able to be removed from an olefinic substrate. Preferably, the anion $Z^-$ comprises one or more boron atoms. More preferably, the anion $Z^-$ is an anion of the formula $BAr^{(-)}_4$, wherein substituents Ar, the same or different from each other, are aryl radicals such as phenyl, pentafluorophenyl, bis (trifluoromethyl)phenyl. Particularly preferred is the tetrakis-pentafluorophenyl borate. Furthermore, compounds of formula $BAr_3$ can be suitably used.

Particularly suitable catalysts according to the invention are those comprising the product of the reaction between di(n-butyl) silandiylbis(fluorenyl)zirconium dichloride and a methylalumoxane.

The catalysts used in the process of the present invention can be also used on inert supports. This is obtained by depositing the metallocene (A), or the product of the reaction of the same with the component (B), or the component (B) and thereafter the metallocene (A), on inert supports such as for example silica, alumina, styrene-divinylbenzene copolymers, polyethylene or polypropylene.

The solid compound thus obtained, combined with a further addition of alkylaluminium compound either as such or prereacted with water, if necessary, is usefully used in the gas phase polymerization.

Catalysts of the present invention are useable in the polymerization reaction of olefins.

Still further the present invention relates to a process for the polymerization of olefins comprising the polymerization reaction of at least an olefinic monomer in the presence of a catalyst as above described.

In particular, catalysts according to the invention can be suitably used in the homopolymerization reaction of alpha-olefins such as ethylene, propylene or 1-butene. Another use of interest of the catalysts of the invention is in the copolymerization reactions of ethylene with alpha-olefins such as propylene and 1-butene.

A particularly interesting use of the catalysts of the invention is the polymerization of propylene. The propylene polymers obtainable with the present catalysts are endowed with an atactic structure and, therefore, they are substantially amorphous. Their melting enthalpy ($\Delta H_f$) is generally not measurable.

The molecular weights of the aforementioned propylene polymers are generally of industrial interest. Their intrinsic viscosities is generally higher than 1.0 dl/g, preferably higher than 1.5, more preferably higher than 2.0 dl/g.

The molecular weights of the propylene polymers, in addition to being high, are distributed over relatively limited ranges. An index of molecular weight distribution is represented by the ratio $M_w/M_n$ which is preferably less than 4, more preferably less than 3.

$^{13}$C-N.M.R. analysis gives information on the tacticity of the polymeric chain, that is the distribution of the relative configuration of the tertiary carbons.

The structure of the aforementioned propylene polymers is substantially atactic. It is observed that the syndiotactic diads (r) are more numerous than the isotactic diads (m). Generally, the value of the relation %r-%m is higher than 0, particularly higher than 5, more particularly higher than 10.

The Bernoullianity index (B), defined as:

$$B=4[mm][rr]/[mr]^2$$

has values near to the unit, generally comprised in the range 0.7–1.3, preferably comprised in the range 0.8–1.2.

The possibility of obtaining directly, as the only product of the polymerization reaction of propylene, a substantially amorphous polypropylene endowed with high molecular weight represents an advantage over the traditional processes.

The process of the polymerisation of olefins according to the invention may be carried out in liquid phase, optionally in the presence of an inert hydrocarbon solvent, or in gas phase. The hydrocarbon solvent may be aromatic such as toluene, or aliphatic, such as propane, hexane, heptane, isobutane, cyclohexane.

The polymerization temperature in processes for the ethylene or propylene homopolymerization is generally comprised between—50° C. and 250° C., in particular between 20° C. and 90° C.

The molecular weight of the polymers can be varied merely by varying the polymerization temperature, the type or the concentration of the catalytic components or by using molecular weight regulators.

The molecular weight distribution can be varied by using mixtures of different metallocenes, or carrying out the polymerization in more steps differing as to polymerization temperatures and/or concentrations of the molecular weight regulator.

Polymerization yields depend on the purity of the metallocene component of the catalyst. Therefore, in order to increase the yields of polymerization, metallocenes are generally used after a purification treatment. A major advantage of the metallocenes of the invention over those of the prior art is represented by their higher solubilities, allowing to obtain them in highly purified form and, consequently, to increase the polymerization yields to a significative extent.

The components of the catalyst can be contacted among them before the polymerization. The contact time is generally comprised between 1 minute and 24 hours. The precontacted components can be suitably brought to dryness and used in polymerization as a powder, optionally in admixture with suitable dispersing agents such as waxes or oils.

Figure 1:
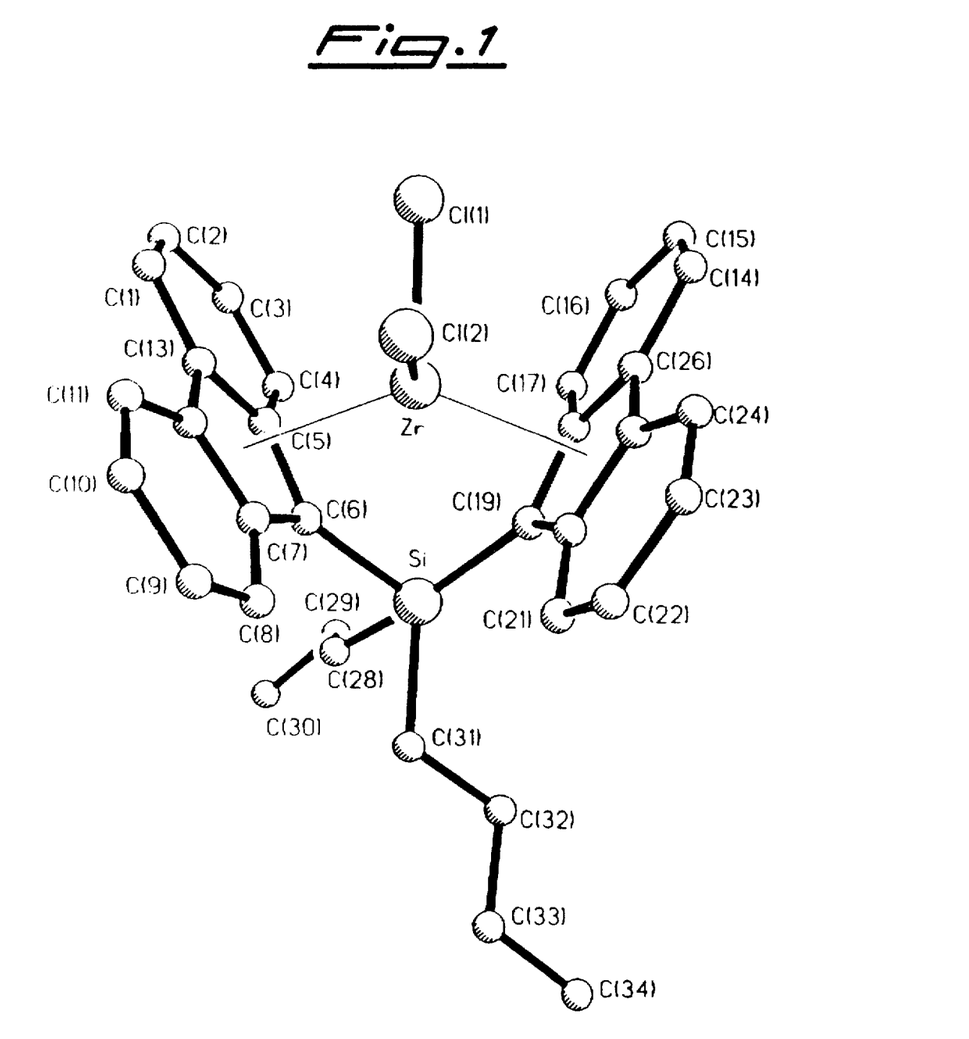
FIG. 1 is a computer generated diagram of a metallocene according to the invention.

FIG. 1 reports a computer generated diagram of the metallocene prepared in Example 2 based on X-ray crystallography data.

The following examples are given to illustrate and not to limit the invention.

CHARACTERIZATIONS

The intrinsic viscosity [η] was measured in tetrahydronaphtalene at 135° C.

The Differential Scanning Calorimetry (DSC) measurements were carried out on an apparatus DSC-7 of Perkin-Elmer Co. Ltd. according to the following procedure. About 10 mg of sample were heated at 200° C. with a scanning speed equal to 20° C./minute; the sample was kept at 200° C. for 5 minutes and thereafter was cooled with a scanning speed equal to 20° C./minute. Thereafter a second scanning equal to 20° C./min was carried out according to the same modalities of the first one. The values reported are those obtained in the second scanning.

The $^1$H-N.M.R. analysis of the polymer have been carried out on a Bruker AC200 instrument at 200.133 MHz, using $CDCl_3$ as solvent at room temperature.

PREPARATIONS OF THE METALLOCENES

EXAMPLE 1

Synthesis of di(n-butyl)bis(9-fluorenyl)silane

Fluorene (23.27 g, 140 mmol) was dissolved in 100 mL diethyl ether and the solution was cooled to −78° C. Methyllithium (1.4 M in diethyl ether, 140 mL) was added dropwise to the stirred solution while maintaining the temperature at −78° C. After the addition was complete, the solution was allowed to warm to room temperature. Stirring was continued overnight. In a separate flask, di-n-butyldichlorosilane (14.9 g, 70 mmol) was dissolved in 50 mL diethyl ether. The temperature was reduced to −78° C., and the solution (prepared above) containing the fluorene anion was added to this stirred solution, dropwise. After the addition was complete, the reaction was allowed to warm slowly to room temperature and stirred overnight. The reaction was then treated with a saturated solution of ammonium chloride, the organic layer was collected and dried over magnesium sulfate, and dried in vacuo. The material was further purified by washing with methanol and drying in vacuo. Yield: 23.39 g (70.7%, 97% purity by GCMS). $^1$H-NMR ($CD_2Cl_2$), d, ppm: 7.81 (d, 4H), 7.30 (m, 12H), 3.95(s, 2H), 1.05(m, 4H), 0.85(m, 10H), 0.5(m, 4H).

EXAMPLE 2

Synthesis of di(n-butyl)silanediylbis(9-fluorenyl)zirconium dichloride - $Bu_2SiFlu_2ZrCl_2$ Di(n-butyl)bis(9-fluorenyl)silane (4.72 g, 10 mmol) was dissolved in 100 mL of $Et_2O$ and the temperature was lowered to −78 ° C. Methyllithium (20 mmol, 1.4M in $Et_2O$, 14.2 mL) was added dropwise to the stirred solution. After the addition was complete, the reaction was allowed to warm to room temperature and stirring was continued overnight.

In a separate flask $ZrCl_4$ (2.33 g, 10 mmol) was slurried in 70 mL of pentane and the temperature was then lowered to −78° C. The dianion prepared above was added in a dropwise fashion. After the addition was complete, the reaction was allowed to warm to room temperature and stirring was continued overnight. The solids were then collected by filtration, washed with fresh $Et_2O$. The product was than repeatedly washed with $CH_2Cl_2$ and collected by filtration. $CH_2Cl_2$ was removed in vacuo, leaving a bright red free-flowing powder. Yield 5.54 g (74%) of di(n-butyl) silanediylbis(9-fluorenyl)zirconium dichloride.

$^1$H NMR (300 MHz, $CD_2Cl_2$, δ, ppm): 7.85 (d, 8H), 7.35 (t, 4H), 7.10 (t, 4H), 2.3 (m, 4H), 2.10 (m, 4H), 1.9 (m, 4H), 1.05 (m, 6H).

EXAMPLE 3

Synthesis of di(n-butyl)silanediylbis(9-fluorenyl)hafnium dichloride—$Bu_2SiFlu_2HfCl_2$ Di-n-butlybis(9-fluorenyl)silane (4.72g, 10 mmol) was dissolved in 100 mL diethyl ether and the temperature was lowered to −78° C. Methyllithium (20 mmol, 1.4 M in $Et_2O$, 14.28 mL) was added dropwise to the stirred solution. After the addition was complete, the reaction was allowed to warm to room temperature and stirring was continued overnight. The next morning, the ether was removed in vacuo, and the solids were washed with fresh pentane. Hafnium tetrachloride (3.2 g, 10 mmol) was added as a dry powder and the solids were re-suspended in fresh pentane. The reaction mixture was stirred overnight, after which time the pentane was removed in vacuo, treated with methylene chloride, filtered, and the methylene chloride removed in vacuo producing the product as a bright orange powder. Yield: 1.25 g (17.4%) $^1$-NMR ($CD_2Cl_2$), d, ppm: 7.81 (d, 4H), 7.85 (d, 4H), 7.3–7.4 (t, 4H), 7.0–7.1 (t, 4H), 2.2–2.3 (m, 4H), 1.9–2.1 (m, 4H), 1.7–1.9 (m, 4H), 1.1–1.15 (m, 6H).

EXAMPLE 4

Synthesis of di(n-butyl)silanediylbis(9-fluorenyl)zirconium dimethyl—$Bu_2SiFlu_2ZrMe_2$ To a stirred solution containing 1.58g (2.5 mmol) of the di-n-butyl bis fluorene zirconium dichloride in 75 mLs diethyl ether at −78° C., was added 5 mmol MeLi (3.57 mL of a 1.4M solution in diethyl ether). The solution was stirred overnight, allowing the temperature to warm to ambient slowly overnight. The next morning, the solvents were removed in vacuo, the dark brown solids were taken up in methylene chloride and filtered. The methylene chloride was then removed in vacuo, leaving 0.96 g of a dark brownish red free flowing solid. Yield: 64%; $^1$H-NMR indicates ~90% purity. $^1$H-NMR: d; ppm 7.9 (d, 4H), 7.65 (d, 4H), 7.3(t, 4H), 7.05 (t, 4H), 2.0 (m, 8H), 1.7 (m, 4H), 1.05 (t, 6H), −2.5(s, 6H). note that the ratio of monomethyl to the dimethyl complexes is calculated from the integral heights of the singlet at −2.1 (dimethyl integration is 20 mm, monomethyl is 2 mm).

EXAMPLE 5

Synthesis of n-hexylmethylbis(9-fluorenyl)silane

Fluorene (50.73 g, 0.305 mol) was dissolved in 250 mL of dry THF in a one liter Schlenk flask equipped with an addition funnel and attached to a nitrogen line. The temperature of the fluorene solution was lowered to −78° C. under a positive nitrogen pressure and methyllithium (0.305 mol, 218 mL) was added dropwise via the addition funnel. Once addition was complete the temperature of the stirring solution was allowed to rise to room temperature. The solution was then stirred overnight. Excess solvent was removed under vacuum. The residual fluorene anion was washed with 300 mL of dry hexane in a nitrogen drybox.

n-Hexylmethyldichlorosilane (30.4 g, 0.152 mol) and 300 mL of dry THF were charged to a one liter Schlenk equipped with an addition funnel. Fluorene anion (52.4 g, 0.305 mol) was dissolved in approximately 200 mL of dry THF and charged to the addition funnel. The temperature of the stirring solution was lowered to −78° C. under positive nitrogen pressure. The fluorene anion was added dropwise over two hours. After the anion addition was complete, the reaction mixture was allowed to warm to room temperature. The solution was allowed to stir overnight. The solution was washed with three 200 mL aliquots of water, retaining the organic layer after each washing. The organic layer was dried with magnesium sulfate and filtered. The product was recrystallized from hexane. The yield of this reaction is 19.6%.

EXAMPLE 6
Synthesis of n-hexylmethylsilanediylbis(9-fluorenyl) zirconium dichloride—MeHexSiFlu$_2$ZrCl$_2$ n-Hexylmethylbisfluorenylsilane (5 mmol, 2.3g) was dissolved in 50 mL diethyl ether and the temperature was lowered to -78° C. Dropwise methyllithium (10 mmol, 1.4 M solution in diethyl ether, 7.2 mL)was added. After addition was complete, the flask and contents were allowed to warm to room temperature slowly overnight, after which time the dianion prepared in this fashion was added to a stirred flask containing ZrCl$_4$ (5 mmol, 1.16 gms) in a pentane slurry at -78° C. The flask and contents were allowed to slowly warm to room temperature overnight, after which time the solvents were evaporated in vacuo. The compound was filtered from a methylene chloride solution, and dried in vacuo. Yield 2.14 gms (69%) of a dark red free flowing powder.

EXAMPLE 7
Synthesis of n-octylmethylbis(9-fluorenyl)silane

Fluorene (47.80 g, 0.288 mol) was dissolved in 300 mL of dry THF in a one liter Schlenk flask equipped with an addition funnel and attached to a nitrogen line. The temperature of the fluorene solution was lowered to -78° C. under a positive nitrogen pressure and methyllithium (0.288 mol, 205 mL) was added dropwise via the addition funnel. Once addition was complete the temperature of the stirring solution was allowed to rise to room temperature. The solution was then stirred overnight. Excess solvent was removed under vacuum. The residual fluorene anion was washed with 300 mL of dry hexane in a nitrogen drybox.

n-Octylmethyldichlorosilane (32.68 g, 0.144 mol) and 200 mL of dry THF were charged to a one liter Schlenk flask equipped with an addition funnel. Fluorene anion (49.50 g, 0.288 mol) was dissolved in approximately 200 mL of dry THF and charged to the addition funnel. The temperature of the stirring solution was lowered to -20° C. under positive nitrogen pressure. The fluorene anion was added dropwise over two hours. After the addition of anion was complete the reaction mixture was allowed to warm to room temperature. The solution was then stirred overnight. The solution was washed with three 200 mL aliquots of water, retaining the organic layer after each washing. The organic layer was dried with magnesium sulfate and filtered. The product was recrystallized from a diethyl ether/methanol solution. The yield of this reaction is 10%.

EXAMPLE 8
Synthesis of n-octylmethylsilylbis (9-fluorenyl) zirconium dichloride—MeOctSiFlu$_2$ZrCl$_2$ 4.86 g n-octylmethylbis(9-fluorenyl)silane (10 mmol) was dissolved in 70 mL Et$_2$O. The temperature was lowered to -78° C. and 20 mmol methyllithium was added dropwise, as a 1.4M solution in diethylether (14.3 mL). Stirring was continued overnight and the flask and contents were allowed to warm slowly to room temperature. The dianion was isolated by removing the solvents in vacuo and washing the viscous dark yellow dianion with fresh pentane. The dianion was then re-slurried in fresh pentane, and a slurry containing 10 mmol (2.33 g) ZrCl$_4$ in 20 mL pentane was added dropwise at room temperature. After addition was complete, the flask and contents were stirred overnight. Solvents were then removed by filtration, and the solids were slurried with methylene chloride and filtered. The dark red solution containing the catalyst complex was evaporated to dryness, and washed with fresh pentane, then dried. 5.13 gms of a dark red free flowing powder were isolated in this fashion.

EXAMPLE 9
Synthesis of (2-bicycloheptyl)methylbis(9-fluorenyl)silane

Fluorene (49.6 g, 0.2986 mol) was dissolved in 300 mL of dry diethyl ether in a one liter Schlenk flask equipped with an addition funnel and attached to a nitrogen line. The temperature of the fluorene solution was lowered to -78° C. under a positive nitrogen pressure and methyllithium (0.2986 mol, 213 mL) was added dropwise via the addition funnel. Once addition was complete the temperature of the stirring solution was allowed to rise to room temperature. The solution was then stirred overnight. Excess solvent was removed under vacuum. The residual fluorene anion was washed with 300 mL of dry hexane in a nitrogen drybox.

(2-bicycloheptyl)methyldichlorosilane (31.2 g, 0.1493 mol) and 300 mL of dry diethyl ether were charged to a one liter Schlenk flask equipped with an addition funnel. Fluorene anion was charged to the addition funnel. The temperature of the stirring solution was lowered to -78° C. under positive nitrogen pressure. The fluorene anion was added dropwise over two hours. The solution temperature was allowed to warm to room temperature when anion addition was complete. The solution was then stirred for 72 hours. The solution was washed with one 200 mL aliquot of water added dropwise over 30 minutes. The desired product, a yellowish-white powder precipitated out of solution as the water was added.

EXAMPLE 10
Synthesis of (2-bicycloheptyl)methylsilylbis(9-fluorenyl) zirconium dichloride (2-cycloheptamethylsilyl) bisfluorene (2.34 g, 5 mmol) was slurried in 100 mL diethyl ether and the temperature reduced to -78° C. A 1.4 mmol solution of methyllithium was added dropwise (7.14 mL) and the reaction allowed to slowly warm to room temperature overnight. The dianion slurry was then cannulated into a flask containing 5 mmol ZrCl$_4$ slurried in 50 mL pentane at -78° C. The reaction was stirred overnight and the contents of the flask were allowed to slowly warm to room temperature overnight. The solvents were then removed under vacuum, and the solids slurried and filtered from methylene chloride. The methylene chloride was removed under vacuum and 1.17 gms of a dark red free flowing powder were recovered (yield=38%). Crystals suitable for structural determination were grown from hot toluene solution that were slowly cooled over a 24 hour period.

EXAMPLE 11
Synthesis of 3,3,3-trifluoropropyl(methyl)bis(9-fluorenyl)silane

Fluorene (50.00 g, 0.3008 mol) was dissolved in 350 mL of dry diethyl ether in a one liter Schlenk flask equipped with an addition funnel and attached to a nitrogen line. The temperature of the stirring fluorene solution was lowered to -78° C. under a positive nitrogen pressure and methyllithium (0.3010 mol, 215 mL) was added dropwise via the addition funnel. Once addition was complete the temperature of the reaction mixture was allowed to rise to room temperature. The solution was then stirred until gas evolution had ceased for three hours. 3,3,3-trifluoropropyl (methyl)dichlorosilane (31.75 g, 0.301 mol) and 300 mL of dry diethyl ether were charged to a one liter Schlenk flask equipped with an addition funnel. Fluorene anion was charged to the addition funnel. The temperature of the stirring solution was lowered to −78° C. under positive nitrogen pressure. The fluorene anion was added dropwise over two hours. After addition of the anion was complete the reaction mixture was allowed to warm to room temperature. The solution was then stirred overnight. The solution was washed with three 200 mL aliquots of water, retaining the organic layer after each washing. The organic layer was dried with magnesium sulfate and filtered. The product was recrystallized from hexane. The yield of this reaction is 50.5%.

EXAMPLE 12

Synthesis of 3,3,3-trifluoropropyl(methyl)silanediylbis(9-fluroenyl) zirconium dichloride 3,3,3-trifluoropropyl(methyl)bisfluorenylsilane (1.11 g, 2.4 mmol) was dissolved in 60 mL diethylether and the temperature was lowered to −78° C. with an acetone/dry ice slush bath. Methyllithium (4.8 mmol, 1.4 M diethylether solution, 3.4 mL) was added dropwise to the stirred solution. After addition was complete, the flask and contents were allowed to warm to room temperature overnight. In a separate flask, zirconium tetrachloride (0.56 g, 70 mL) was slurried in 70 mL pentane. The temperature of this slurry was then reduced to −78° C., and the dianion (prepared above) was added dropwise. After addition was complete, the flask and contents were allowed to warm to room temperature overnight. The next morning, the solvents were srmoved from the reaction flask in vacuo, and the solids were treated with methylene chloride, filtered, and the filtrate collected and dried in vacuo. In this fashion 0.933 g of a free flowing red powder were isolated. Crystalline materials suitable for X-ray diffraction studies were grown by the slow evaporation of a methylene chloride solution amade from the reaction products.

POLYMERIZATIONS
Methylalumoxane (MAO)

A commercial (Witco, MW 1400) 30% toluene solution of MAO was dried in vacuo until a solid, glassy material was obtained which was finely crushed and further treated in vacuo until all volatiles were removed (4–6 hours, 0.1 mmHg, 40°–50° C.) to leave a white, free-flowing powder. Modified-methylalumoxane (M-MAO)

The commercial (Ethyl) isopar C solution (62 g Al/L) was used as received.

EXAMPLES 13–18

In a 1-L jacketed stainless-steel autoclave, equipped with a helical, magnetically driven stirrer, a 35-mL stainless-steel vial and a thermoresistance, connected to a thermostat for temperature control, previously washed with a solution of AliBu$_3$ in hexane and then dried at 60° C. under a nitrogen stream, were charged 400 mL of propylene. The autoclave was then thermostatted at 48° C.

The catalyst/cocatalyst mixture was prepared by dissolving the proper amount of metallocene with the methylalumoxane solution (in toluene in the case of MAO or as the commercial solution in isopar-C in the case of M-MAO), obtaining an intensely colored solution which was stirred for 10 min at ambient temperature and then injected into the autoclave at the polymerization temperature in the presence of the monomer.

The catalyst/cocatalyst mixture prepared as described above was injected in the autoclave by means of propylene pressure through the stainless-steel vial, the temperature rapidly brought to 50 ° C. and the polymerization carried out at constant temperature for 1 hour.

The polymerization conditions and relative characterisation data of the polymer obtained are reported in Table 1. From DSC analysis, no peaks were observed attributable to the melt enthalpy.

EXAMPLE 19
(COMPARISON)

It was worked according to the procedure of examples 13–19, but operating with a 2.3-L autoclave in which 1000 mL of propylene were charged, and using dimethylsilanediylbis(9-fluroenyl) zirconium dichloride prepared as in Example 1 of EP-A-604,908 instead of di(n-butyl) silanediyl-bis(9-fluorenyl) zirconium dichloride.

The polymerization conditions and relative characterisation data of the polymer obtained are reported in Table 1. From DSC analysis, no peaks were observed attributable to the melting enthalpy.

EXAMPLES 20–21
(COMPARISON)

It was worked according to the procedure of examples 13–19, butusingdimethylsilanediylbis(9-fluorenyl) zirconiumdichloride prepared as in Example 1 of EP-A-604,908 instead of di(n-butyl) silanediylbis(9-fluorenyl)zirconium dichloride.

The polymerization conditions and relative characterisation data of the polymer obtained are reported in Table 1. From DSC analysis, no peaks were observed attributable to the melting enthalpy.

TABLE 1

| EXAMPLE | metallocene type | (mgrams) | Cocatalyst | Al/Zr (mol) | yield (grams) | activity (Kg$_{pol}$/g$_{met}$h) | I.V. (dL/g) |
|---|---|---|---|---|---|---|---|
| 13 | Bu$_2$SiFlu$_2$ZrCl$_2$ | 1 | MAO | 2000 | 51.75 | 51.75 | 2.76 |
| 14 | Bu$_2$SiFlu$_2$ZrCl$_2$ | 1 | M-MAO | 2000 | 54.85 | 54.85 | 2.44 |
| 15 | Bu$_2$SiFlu$_2$ZrCl$_2$ | 1 | M-MAO | 2000 | 60.25 | 60.25 | 2.35 |
| 16 | Bu$_2$SiFlu$_2$ZrCl$_2$ | 0.5 | M-MAO | 1000 | 53.44 | 106.88 | 2.61 |
| 17 | MeHexSiFlu$_2$ZrCl$_2$ | 0.5 | M-MAO | 1000 | 24.94 | 49.87 | 2.47 |
| 18 | MeOctSiFlu$_2$ZrCl$_2$ | 0.5 | M-MAO | 1000 | 31.34 | 62.68 | 2.58 |
| 19 CONFR. | Me$_2$SiFlu$_2$ZrCl$_2$ | 4 | MAO | 2355 | 102.86 | 25.71 | 2.57 |
| 20 CONFR. | Me$_2$SiFlu$_2$ZrCl$_2$ | 0.87 | M-MAO | 2340 | 27.25 | 31.33 | 2.30 |
| 21 CONFR. | Me$_2$SiFlu$_2$ZrCl$_2$ | 1 | M-MAO | 2000 | 30.72 | 30.72 | — |

What is claimed is:

1. A metallocene compound of formula (I):

(I)

wherein each $R^1$, same or different, is a hydrogen atom, a $C_1$–$C_{20}$—alkyl cycloalkyl radical, a $C_2$–$C_{20}$—alkenyl radical, a $C_6$–$C_{20}$ aryl radical, a $C_7$–$C_{20}$—alkylaryl radical, or a $C_7$–$C_{20}$ arylalkyl radical, and further wherein two adjacent $R^1$ substituents can form a cycle comprising from 5 to 8 carbon atoms, and furthermore the $R^1$ substituents can contain silicon or germanium atoms;

E is a bridging group selected from the group consisting of an $SiR^3{}_2$ group and a $GeR^3{}_2$ group, wherein each $R^3$, same or different, is a $C_3$–$C_{20}$—alkyl radical, a $C_3$–$C_{20}$—cycloalkyl radical, a $C_2$–$C_{20}$—alkenyl radical, a $C_7$–$C_{20}$—alkylaryl radical, or a $C_7$—$C_{20}$ arylalkyl radical, optionally containing heteroatoms, or the two $R^3$ substituents can be joined to form a cycle comprising up to 8 atoms, at least four total carbon atoms being contained in the two $R^3$ substituents;

M is an atom of a transition metal selected from those belonging to Group 4 and 5 in the Periodic Table of the Elements (new IUPAC version);

each Z substituent, same or different, is a halogen atom, an —OH, —SH, —$R^4$ $OR^4$, —$SR^4$, —$NR^4{}_2$, or —$PR^4{}_2$ group, wherein $R^4$ has the same definition as $R^1$.

2. The metallocene compound according to claim 1, wherein the Rhu 1substituents are hydrogen atoms.

3. The metallocene compound according to claim 1, wherein E is a bis(n-butyl) silanediyl group.

4. The metallocene compound according to claim 1, wherein the Z substituents, same or different, are chlorine atoms or methyl groups.

5. A process for the preparation of a metallocene compound according to claim 1, comprising the following steps:

(a) the reaction of a compound of formula (II):

(II)

wherein substituents $R^1$, same or different from each other, are as defined in claim 1, with a compound able to form the anion of formula (III):

(III)

and thereafter with a compound of formula $EX_2$, wherein E is defined as in claim 1, and substituents X, same or different from each other, are halogen atoms, obtaining a compound of formula (IV):

(IV)

(b) reacting the compound of formula (IV) with a compound able to form the dianion of formula (V):

(V)

and thereafter with a compound of formula $MX'_4$, wherein M is defined as in claim 1, and the substituents X' are halogen atoms, obtaining a compound of formula (VI):

(VI)

(c) when at least one substituent Z from the metallocene of formula (I) is to be different from a halogen, the substitution of at least one substituent X' in the compound of formula an with at least one Z substituent different from halogen.

6. The process according to claim 5, wherein the compound of formula $MX'_4$ is zirconium tetrachloride.

* * * * *